US008353883B2

(12) United States Patent
Johnson et al.

(10) Patent No.: US 8,353,883 B2
(45) Date of Patent: Jan. 15, 2013

(54) ELASTOMERIC GLOVE CONTAINING A FOAM DONNING LAYER

(75) Inventors: David W. Johnson, Alpharetta, GA (US); Martin Shamis, Alpharetta, GA (US); Alison Salyer Bagwell, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 916 days.

(21) Appl. No.: 11/303,003

(22) Filed: Dec. 15, 2005

(65) Prior Publication Data
US 2007/0136926 A1 Jun. 21, 2007

(51) Int. Cl.
*A61M 35/00* (2006.01)
*A41D 19/00* (2006.01)
*B05D 3/00* (2006.01)

(52) U.S. Cl. ......... 604/292; 604/290; 604/293; 427/2.3; 2/159; 2/161.6; 2/161.7; 2/161.8; 2/164; 2/167; 2/168

(58) Field of Classification Search .................. 604/292, 604/289; 2/159, 161.6, 161.7, 168; 223/78, 223/79
See application file for complete search history.

(56) References Cited

U.S. PATENT DOCUMENTS

| | | | |
|---|---|---|---|
| 2,683,730 A | 7/1954 | Seeger et al. | |
| 3,342,182 A * | 9/1967 | Charos | 604/292 |
| 3,903,232 A | 9/1975 | Wood et al. | |
| 4,137,200 A | 1/1979 | Wood et al. | |
| 4,186,445 A * | 2/1980 | Stager | 2/164 |
| 4,193,135 A * | 3/1980 | Rhee | 2/162 |
| 4,355,424 A * | 10/1982 | McCoy, Jr. | 2/16 |
| 4,377,160 A * | 3/1983 | Romaine | 602/2 |
| 4,393,871 A | 7/1983 | Vorhauer et al. | |
| 4,517,326 A | 5/1985 | Cordts et al. | |
| 4,773,409 A * | 9/1988 | Cilento et al. | 602/49 |
| 5,065,752 A | 11/1991 | Sessions et al. | |
| 5,147,338 A * | 9/1992 | Lang et al. | 604/304 |
| 5,274,846 A * | 1/1994 | Kolsky | 2/460 |
| 5,296,518 A | 3/1994 | Grasel et al. | |
| 5,317,760 A * | 6/1994 | Best | 2/161.7 |
| 5,614,202 A * | 3/1997 | DeFina | 424/402 |
| 5,650,225 A * | 7/1997 | Dutta et al. | 428/318.4 |
| 5,650,450 A | 7/1997 | Lovette et al. | |

(Continued)

FOREIGN PATENT DOCUMENTS

GB 1507232 A * 3/1973
(Continued)

OTHER PUBLICATIONS

Online encyclopedia article "Foam" accessed Jan. 26, 2009. http://en.wikipedia.org/wiki/Foam.*

(Continued)

*Primary Examiner* — Leslie Deak
*Assistant Examiner* — Adam Marcetich
(74) *Attorney, Agent, or Firm* — Dority & Manning, P.A.

(57) ABSTRACT

Elastomeric articles, such as gloves are disclosed. The gloves include a primary matrix made from one or more elastomeric materials and a foam donning layer. In one embodiment, for instance, the donning layer can be formed from a polyurethane foam. The polyurethane foam can be created from the reaction product of a polyurethane prepolymer and a solution containing water. The resulting foam can be hydrophilic and can absorb moisture for preventing moisture from being trapped between the primary matrix and a user's skin.

15 Claims, 3 Drawing Sheets

U.S. PATENT DOCUMENTS

| | | | |
|---|---|---|---|
| 5,673,437 A * | 10/1997 | Chase et al. | 2/167 |
| 5,819,312 A * | 10/1998 | Snyder et al. | 2/16 |
| 6,013,344 A | 1/2000 | Corbins | |
| 6,265,016 B1 | 7/2001 | Hostettler et al. | |
| 6,461,626 B1 | 10/2002 | Rabe et al. | |
| 6,514,504 B1 | 2/2003 | Yen et al. | |
| 6,531,142 B1 | 3/2003 | Rabe et al. | |
| 6,558,682 B2 | 5/2003 | Yen et al. | |
| 6,566,576 B1 | 5/2003 | Komerska et al. | |
| 6,617,014 B1 | 9/2003 | Thomson | |
| 6,759,220 B1 | 7/2004 | LeJeune et al. | |
| 6,920,881 B2 | 7/2005 | Narula et al. | |
| 6,991,848 B2 | 1/2006 | Thomason | |
| 7,713,252 B2 * | 5/2010 | Greene et al. | 604/292 |
| 2002/0018884 A1 | 2/2002 | Thomason | |
| 2002/0182245 A1 | 12/2002 | Thomson | |
| 2003/0090037 A1 | 5/2003 | Woodford et al. | |
| 2003/0118837 A1 * | 6/2003 | Modha et al. | 428/423.1 |
| 2003/0124318 A1 | 7/2003 | Magill et al. | |
| 2003/0167556 A1 * | 9/2003 | Kelley | 2/206 |
| 2004/0089320 A1 | 5/2004 | Williams et al. | |
| 2004/0098786 A1 * | 5/2004 | Hottner et al. | 2/159 |
| 2004/0126558 A1 | 7/2004 | Williams et al. | |
| 2004/0131838 A1 * | 7/2004 | Serra et al. | 428/304.4 |
| 2004/0191280 A1 * | 9/2004 | Nakajima et al. | 424/401 |
| 2004/0200094 A1 * | 10/2004 | Baychar | 36/55 |
| 2004/0250340 A1 * | 12/2004 | Piper et al. | 2/411 |
| 2005/0003178 A1 | 1/2005 | Detert et al. | |
| 2005/0019083 A1 | 1/2005 | Williams et al. | |
| 2005/0037058 A1 | 2/2005 | Canada et al. | |
| 2005/0045201 A1 | 3/2005 | Williams | |
| 2005/0136236 A1 | 6/2005 | Hassan et al. | |
| 2005/0147654 A1 | 7/2005 | Matloub et al. | |
| 2005/0186260 A1 * | 8/2005 | Narini et al. | 424/445 |
| 2005/0221073 A1 * | 10/2005 | Liou | 428/304.4 |
| 2005/0257805 A1 | 11/2005 | Williams | |
| 2005/0281988 A1 * | 12/2005 | McCormick | 428/190 |
| 2006/0013963 A1 | 1/2006 | Thomason | |
| 2006/0064066 A1 * | 3/2006 | Wang | 604/292 |
| 2006/0247585 A1 * | 11/2006 | Kelly | 604/290 |

FOREIGN PATENT DOCUMENTS

| | | |
|---|---|---|
| GB | 2357286 | 6/2001 |
| WO | WO 03057750 A1 | 7/2003 |
| WO | WO 2005060855 A1 | 7/2005 |

OTHER PUBLICATIONS

Online encyclopedia article "Jojoba oil" accessed Tuesday, Jul. 14, 2009. http://en.wikipedia.org/wiki/Jojoba_oil.*

Online article "Industry News," Advances in Skin & Wound Care: Jul./Aug. 2002—vol. 15—Issue 4—p. 150, 152. Accessed Jan. 6, 2010. http://journals.lww.com/aswcjournal/Fulltext/2002/07000/Industry_News.2.aspx.*

PCT Search Report for International Application No. PCT/US2006/033328 dated Feb. 28, 2007.

Product Information 13 Hydrophilic PrePolymers (PrePal™) from Lendell Manufacturing, Inc., 2 pages.

Product Information—Medical Grade Foam (Medi Sponge® and Microbisan™) from Lendell Manufacturing, Inc., 2 pages.

* cited by examiner

ELASTOMERIC GLOVE CONTAINING A FOAM DONNING LAYER

BACKGROUND OF THE INVENTION

Elastomeric materials have been formed into countless different articles suitable for use in many applications. For instance, elastomeric materials have been commonly used to produce various glove products, such as surgical gloves, examination gloves, gloves for use in clean room applications, gloves used for cleaning and disinfecting surfaces, and the like. Elastomeric materials have been found particularly well suited for constructing gloves due to their physical characteristics. For example, elastomeric materials, in addition to having good elastic properties, exhibit good strength characteristics and may be produced so as to be impermeable not only to aqueous solutions, but also to many solvents and oils.

Depending upon the particular use and application, gloves can be worn by a user for a substantial period of time. For instance, healthcare workers wear medical exam gloves during just about any procedure where they are in contact with a patient or a patient's bodily fluids. For example, healthcare workers wear medical examination gloves when changing a dressing, a catheter, a bedpan, bathing a patient, etc. These procedures can take as little as five minutes or can take over an hour to complete. Healthcare workers on average can wear ten to fifteen pairs of gloves per eight-hour shift. Elastomeric gloves, however, typically have a low moisture vapor transmission rate. As such, moisture can become trapped in the glove next to the skin of the wearer. When the skin is occluded for long periods of time, the skin can begin to break down causing skin damage and skin irritation.

In view of the above, various attempts have been made to produce an elastomeric glove that does not trap moisture adjacent to the user's skin. For instance, in the past, some elastomeric gloves have been coated with a cotton flocking. The cotton, however, can produce lint while the glove is being worn making such gloves only useful in very limited applications. For instance, such gloves are typically not well suited to being used as surgical gloves or medical examination gloves.

In view of the above, a need currently exists for an improved elastomeric glove that is capable of removing moisture from the surface of the skin.

SUMMARY OF THE INVENTION

The present disclosure is generally directed to an elastomeric article and to a method for producing the elastomeric article. In one embodiment, for instance, the elastomeric article comprises a glove containing a donning layer made from a foam. The presence of the foam provides the glove with some breathability and, in one embodiment, can be configured to absorb moisture that may be present in between the glove wall and the skin of a user. The foam can also be formed so as to contain an additive, such as an anti-microbial agent, a bacteriostatic agent, a liquid absorption agent, a medicament, a therapeutic agent, mixtures thereof, and the like. The additive can be present in the foam in order to improve the properties of the foam or in order to provide a benefit to the user of the product.

In one embodiment, the glove comprises a primary matrix comprising an elastomeric polymer. The primary matrix can be in the shape of a glove and can include an inside hand-contacting surface. The elastomeric polymer used to form the primary matrix may comprise, for instance, a nitrile polymer, a natural rubber latex polymer, a polyvinyl chloride polymer, a block copolymer and the like. The primary matrix may be formed from one layer of an elastomeric polymer or can be formed from multiple layers.

In accordance with the present disclosure, a foam layer is located on the inside surface of the glove. The foam layer, for instance, may comprise an open cell foam and may be hydrophilic and capable of absorbing moisture.

In one embodiment, the foam layer is formed from a polyurethane foam, such as a polyether polyurethane. For instance, the foam layer may comprise the reaction product of a polyurethane prepolymer with a solution comprising water. The prepolymer may comprise an isocyanate-capped polyoxyethylene polyol. The prepolymer, once contacted with water, undergoes an irreversible chemical reaction and forms the foam. In one embodiment, one or more surfactants may be combined with water and used to contact the prepolymer. The surfactant can be added in order to modify the properties of the foam for the particular application.

In order to form the glove product, a primary matrix may be formed on a former in the shape of a hand. The primary matrix may comprise one or more layers of an elastomeric material. A foam layer is then formed on the primary matrix while the primary matrix remains on the former. The glove is then stripped from the former and turned inside out so that the foam layer is on the hand-contacting surface.

In one embodiment, in order to form the foam layer, the former coated with the primary matrix is first dipped into a prepolymer composition that contains a prepolymer and a diluent to form a prepolymer coating. The prepolymer may comprise a polyurethane prepolymer and the diluent may comprise any suitable non-aqueous diluent. The diluent, for instance, may comprise N,N-dimethylformamide, tetrahydrofuran, toluene, acetone, or the like.

Once the prepolymer coating has been formed on the primary matrix, the prepolymer coating is contacted with a solution comprising water and optionally one or more surfactants. For instance, the solution can be contacted with the prepolymer coating by spraying the solution onto the coating. Alternatively, the former can be dipped into the solution for contacting the solution with the prepolymer coating. Once contacted with the solution, the prepolymer coating forms a foam.

Other features and aspects of the present disclosure are discussed in greater detail below.

BRIEF DESCRIPTION OF THE DRAWINGS

A full and enabling disclosure of the present disclosure, including the best mode thereof to one of ordinary skill in the art, is set forth more particularly in the remainder of the specification, including reference to the accompanying figures in which.

DETAILED DESCRIPTION

It is to be understood by one of ordinary skill in the art that the present discussion is a description of exemplary embodiments only, and is not intended as limiting the broader aspects of the present disclosure, which broader aspects are embodied in the exemplary construction.

The present disclosure is generally directed to a polymer foam coating applied to a surface of an elastomeric article. In one embodiment, the polymer foam coating may be formed on the skin contacting surface of a glove as a donning layer. The foam layer can provide various benefits and advantages. For example, the foam layer may be configured to absorb water for preventing moisture from being trapped next to the skin of a wearer if the glove is worn for extended periods of time. The foam layer can also provide some breathability to the product.

In addition, the foam can be constructed to have various different properties. For instance, the foam can be formed so that the glove may be easier to don. In particular, the foam may have lubricious properties that may make it easier to place the glove on a hand, even if the hand is wet. Also of particular advantage, the foam layer can be constructed so as to carry various additives.

The additives may improve the properties of the foam layer and/or provide a benefit to the skin of a user. For instance, the additive contained within the foam layer may comprise an anti-microbial agent, a bacteriostatic agent, a liquid absorption agent, a medicament, a therapeutic agent, mixtures thereof and the like.

In general, the foam layer present on the hand-contacting surface of the glove can be made from any suitable polymeric material. In many applications, for instance, the foam layer can be hydrophilic and capable of absorbing moisture so that the moisture does not get trapped between the primary matrix of the glove and the skin of a user. The foam material can be made to be somewhat rigid or very soft. In one embodiment, the foam layer can also be made from a lubricious foam material.

In one particular embodiment, the foam layer can be formed on an in-line process. For example, in one embodiment, a prepolymer composition can be coated on the primary matrix of the glove during formation of the glove. After the prepolymer composition is applied to the primary matrix, the prepolymer composition is then contacted with a solution that causes the prepolymer to form a foam. By carefully selecting the prepolymer composition and the aqueous solution that contacts the prepolymer composition, a variety of cell sizes, textures, densities and resiliencies can be produced. Further, as will be described in greater detail below, other additives can be incorporated into the foam that provide other various advantages and benefits.

In one particular embodiment, the foam layer is formed from a polyurethane polymer, such as a polyether polyurethane. The polyurethane can be formed by reacting together a polyurethane prepolymer with a solution comprising water. Polyurethane foams that may be used in accordance with the present disclosure are disclosed, for instance, in U.S. Pat. No. 3,903,232, U.S. Pat. No. 4,137,200, U.S. Pat. No. 5,065,752, U.S. Pat. No. 5,296,518, U.S. Pat. No. 6,566,576, and U.S. Pat. No. 6,759,220, which are all incorporated herein by reference.

For example, the foam layer can be formed from a prepolymer comprising an isocyanate-capped polyoxyethylene polyol. The prepolymer can have a reaction functionality of greater than 2, such as a hydroxyl functionality of at least 2.

During capping, the polyisocyanate may be reacted with the polyol such that the reaction product, i.e. the capped product, is substantially void of reactive hydroxy groups while containing more than two reactive isocyanate sites per average molecule.

The polyoxyethylene polyol used as a reactant in preparing the capped product may have a weight average molecular weight of about 200 to about 20,000, such as between about 600 to about 6,000, with a hydroxyl functionality of about 2 or greater, preferably from about 2 to about 8.

Polyoxyethylene polyol is terminated or capped by reaction with a polyisocyanate. The reaction may be carried out in an inert moisture-free atmosphere such as under a nitrogen blanket, at atmospheric pressure at a temperature in the range of from about 0° C. to about 120° C. for a period of time of up to about 20 hours depending upon the temperature and degree of agitation. This reaction may be effected also under atmospheric conditions provided the product is not exposed to excess moisture. The polyisocyanates used for capping the polyoxyethylene polyol include PAPI (a polyaryl polymethylenepolyisocyanate as defined in U.S. Pat. No. 2,683,730), tolyene diisocyanate, triphenylmethane-4,4',4"-triisocyanate, benzene-1,3,5-triisocyanate, toluene-2,4,6-triisocyanate, diphenyl-2,4,4'-triisocyanate, hexamethylene diisocyanate, xylene diisocyanate, chlorophenylene diisocyanate, diphenylmethane-4,4'-diisocyanate, naphthalene-1,5-diisocyanate, xylene-alpha, 3,3'-dimethyl-4,4'-biphenylene diisocyanate, 3,3'-dimethoxy-4,4'-biphenylene diisocyanate, 2,2',5,5'-tetramethyl-4,4'-biphenylene diisocyanate, 4,4'-methylenebis(phenylisocyanate), 4,4'-sulfonylbis (phenylisocyanate), 4,4'-methylene di-orthotolylisocyanate, ethylene diisocyanate, trimethylenediisocyanate, diicyclohexyl methane-4,4'-diisocyanate, isophorone diisocyanate, 1,6-hexamethylene diisocyanate, 2,2,4-trimethyl-1,6-hexane diisocyanate, and the like. Mixtures of any one or more of the above-mentioned organic isocyanates may be used as desired. The aromatic diisocyanates, aliphatic and cycloaliphatic diisocyanates and polyisocyanates or mixtures thereof which are especially suitable are those which are readily commercially available, have a high degree of reactivity and a relatively low cost.

Examples of suitable di- and polyfunctional isocyanates that may also be used include:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene bis(cyclohexyl isocyanate)
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyanate
2,4-dimethyl-phenylene diisocyanate
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate 9,10-anthracene diisocyanate
4,4'-diisocyanatodibenzyl
3,3'-dimethyl-4,4'-diisocyanatodiphenyl methane
2,6-dimethyl-4,4'-diisocyanatodiphenyl
2,4-diisocyanatostilbene
3,3-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p"-triphenylmethane triisocyanate
trifunctional trimer (isocyanurate) of isophorone diisocyanate
trifunctional bioret of hexamethylene diisocyanate
trifunctional trimer (isocyanurate) of hexamethylene diisocyanate
polymeric 4,4'-diphenylmethane diisocyanate.

Capping of the polyoxyethylene polyol may be effected using stoichiometric amounts of reactants. Desirably, however, an excess of polyisocyanate is used to insure complete capping of the polyol. Thus, the ratio of isocyanate groups to the hydroxyl groups used for capping is between about 1 to about 4 isocyanate to hydroxyl.

In one embodiment, the isocyanate is reacted with a first polyol having a hydroxyl functionality of at least 2 and a second polyol having a hydroxyl functionality in the range of about 3 to 8. In this embodiment, the first polyol is preferably a hydrophilic oxyalkylene polyol containing at least about 40%, and more preferably about 80 to 100%, oxyethylene. The balance should be oxypropylene, oxybutylene, etc. Suitable examples include random ethylene/propylene oxide oligomers which have a number average molecular weight in the range of about 1000-2500 and are hydrophilic, water soluble and liquid at room temperature.

The second polyol provides crosslinking ability and is preferably a generally linear polyol having at least 3, and preferably between 3 and 8 hydroxyl groups. Usually monomeric polyols having 3 to 4 hydroxyl groups per mole are employed. A suitable example of the second polyol is trimethylolpropane.

In another embodiment, the prepolymer can be made from oxyethylene-containing, multifunctional polyols, e.g. triols, tetrols etc. Oxyethylene-containing triols can be prepared by polymerizing ethylene oxide in the presence of a polyfunctional hydroxyl-containing starter component, such as glycerol, trimethylolpropane or trimethylolethane. The molecular weight of these polymeric triols may be varied greatly, depending on the number of moles of ethylene oxide used in the reaction with the starter component. Starter components such as pentaerythritol and sucrose likewise treated with ethylene oxide lead to polymeric polyoxyethylene tetrols and hexols, respectively.

Polyurethane prepolymers that may be used in the present disclosure can be obtained from various commercial sources. For instance, isocyanate-capped polyether prepolymers can include prepolymers sold under the trademark HYPOL. Examples include HYPOL FHP 2000, HYPOL FHP 2002, HYPOL FHP 3000, HYPOL FHP 4000, HYPOL FHP 5000, HYPOL X6100 and HYPOL hydrogel.

HYPOL 2000, HYPOL 2002 and HYPOL 3000 prepolymers are derived from toluene diisocyanate. FHP 2000 and FHP 2002 both have an equivalent weight (per NCO) of 625, an NCO content of 1.60 meq/g and a specific gravity of 1.19. The viscosity of FHP 2000 is 18,500 cps (Brookfield LVF, #4 Spindle, 12 rpm at 25° C.) and that of FHP 2002 is 20,000.

FHP 3000 has an equivalent weight (per NCO) of 425, an NCO content of 2.35 meq/g, a specific gravity of 1.15 and a viscosity (measured as described above) of 10,500. HYPOL hydrogel is likewise derived from toluene diisocyanate. It has an NCO content of 0.5-0.9 meq/g and a viscosity of 10,000 to 12,000 cps at 25° C.

Another example of an isocyanate-capped prepolymer suitable for use in the present invention and derived from toluene diisocyanate is AQUAPOL prepolymer, commercially available from Freeman Chemical Corporation. AQUAPOL prepolymers have an NCO-value of 2.5 to 3.0 and are formed from the reaction of toluene diisocyanate and an organic polyether polyol containing at least 40 percent by weight ethylene oxide adducts as described in U.S. Pat. No. 4,517,326.

A further example of an isocyanate-capped prepolymer suitable for use in the present invention and which is derived from toluene diisocyanate is sold under the trademark TREPOL, and is commercially available from Twin Rivers Engineering. TREPOL prepolymers have an —NCO content of 1.4 milliequivalents per gram and a viscosity at 90° C. of 4,700 cps.

The HYPOL FHP 4000 and HYPOL FHP 5000 prepolymers are derived from methylene diisocyanate. FHP 4000 has an equivalent weight (per NCO) of 476, an NCO content of 2.10 meq/g, a Brookfield viscosity (LVF, #4 Spindle, 12 r.p.m. at 25° C.) of 20,000 and specific gravity of 1.17. FHP 5000 has an equivalent weight (per NCO) of 392, an NCO content of 2.55 meq/g, a Brookfield viscosity (measured as for FHP 4000) of 18,000 and a specific gravity of 1.17.

An example of an isocyanate-capped prepolymer suitable for use in the present invention and derived from isophorone diisocyanate is HYPOL X6100. It has an —NCO content of 1.8 meq/grams and a viscosity at 25° C. of 12,000 cps.

In order to cause the prepolymer to foam, the prepolymer composition is simply combined with a solution containing water. The solution containing water, for instance, may comprise water only, a water slurry or suspension, a water emulsion, or a water solution having water soluble materials included therein. Water can be contacted with the prepolymer composition in weight ratios of prepolymer:water in the range of from about 0.01:1 to about 50:1. In accordance with the present disclosure, the amount of water that is contacted with the prepolymer composition can be carefully controlled in order to control the properties of the resulting foam and the thickness of the foam.

In addition, surfactants may be added to the aqueous solution to adjust the texture and appearance of the foam. For instance, surfactants can be used to control cell size, shape, etc. as well as to control the rigidity of the foam.

Surfactants that may be contained in the aqueous solution include anionic, cationic, and non-ionic surfactants. Examples of anionic surfactants include lauryl sulfate or octyl sulfate. Cationic surfactants that may be used include cetylpyridinium chloride or dodecyltrimethylammonium bromide. Non-ionic surfactants include block copolymers of ethylene oxide and propylene oxide, ethoxylated sorbitan fatty acid esters, glycerol esters, polyglycerol esters and silicone fluids. Non-ionic surfactants that may be used include PLURONIC L 92 or PLURONIC F-88 surfactants obtained from the BASF Corporation of Mount Olive, N.J. It should be understood, however, that various other surfactants may be included in the aqueous solution and that the above list is merely exemplary and not exhaustive.

As described above, the particular type of surfactant selected and the amount of surfactant contained in the aqueous solution can be selected in order to control the properties of the resulting foam. When present, the surfactant may be included in the aqueous solution in an amount from about 0.1% to about 25% by weight, such as from about 0.5% to about 2.5% by weight in the aqueous solution.

Of particular advantage, various additives can be incorporated into the prepolymer composition and/or the aqueous solution when forming the polymer foam. The additives can be incorporated into the materials in order to modify or improve the properties of the foam or to provide a benefit to the user of the product. For example, in one embodiment, a liquid absorption agent may be incorporated into the foam in order to further improve the ability of the foam to absorb moisture. For example, suitable superabsorbent polymers can be incorporated into the prepolymer composition. Such polymers include sodium and aluminum salts of starch grafted copolymers of acrylates and acrylamides and combinations thereof. Other absorbent polymers include various polyacrylate salts.

In other embodiments, the liquid absorption agent may comprise a hydrocolloid. Suitable hydrocolloids include, for instance, natural gums such as arabic gum, ghatti gum, karaya gum, tragacanth gum, guar gum, locust bean gum and acacia gum; seaweed extracts such as agar, algin, alginate salts and carrageenin; cereal gums; starches; fermentation or microbial gums such as dextran gum and xanthan gum; pectins; gelatins; casein; and collagens. Modified forms of the hydrocolloids may also be used, including, for example, the oxidized, acetylated, carboxylated, esterified, methylated, aminated, etherated, sulfated, borated and phosphated derivatives of the hydrocolloid absorptive agents. Suitable synthetic gums include polyvinylpyrrolidone, low methoxyl pectin, propyleneglycol alginates, carboxymethyl locust bean gum and carboxymethyl guar gum.

In other embodiments, the additive incorporated into the polymer foam may comprise a medicament, a therapeutic agent, an anti-microbial agent, a bacteriostatic agent, and the like.

Examples of additives that may be incorporated into the foam include water soluble alcohols including monols, diols, and polyhydric alcohols. Examples of monols include ethyl alcohol and isopropyl alcohol. Exemplary diols include propylene glycol, polyethylene glycol, and polypropylene glycol. Examples of suitable polyhydric alcohols are glycerin, 1,2,4-butane triol, trimethylolpropane, pentaerythritol and sorbitol. Glycerin, for instance, is not only a medicament but also a therapeutic agent.

Examples of other therapeutic agents include various cosmetic agents, bath oils, hand lotions, aloe vera, and the like.

Still other therapeutic agents that may incorporated into the foam layer include emollients such as beeswax, butyl stearate, ceramides, cetyl palmitate, oleyl alcohol, petroleum jelly, glycerol stearate, lanolin, cetearyl alcohol, stearyl alcohol, and derivatives thereof. Other additives include antioxidants such as Vitamin C, Vitamin E and the like, chelating agents such as EDTA and various other skin conditioners such as amino acids, alpha-hydroxy acids, shea butter, and the like.

As described above, in one embodiment, an anti-microbial agent may also be incorporated into the foam layer. In one embodiment, for instance, the anti-microbial agent may comprise a composition containing silver.

One embodiment of a process for forming gloves in accordance with the present disclosure will now be discussed in greater detail.

As described above, the foam layer is formed on the inside hand-contacting surface of the glove. The glove itself is made from one or more elastomeric materials.

For example, the gloves of the present disclosure may be formed of a natural or a synthetic latex or a dissolved elastomeric polymer, as desired. For instance, the gloves of the present disclosure may be formed of a natural rubber, a nitrile rubber, a polyurethane, a homopolymer of a conjugated diene, a copolymer of a least two conjugated dienes, a copolymer of at least one conjugated diene and at least one vinyl monomer, or any other suitable combinations thereof. For example, the glove may be a polyvinyl chloride glove, as is known in the art. Moreover, combinations of polymers or copolymers may be in a single layer of an article or in separate layers, such as in a multi-layer article.

Figure 1:
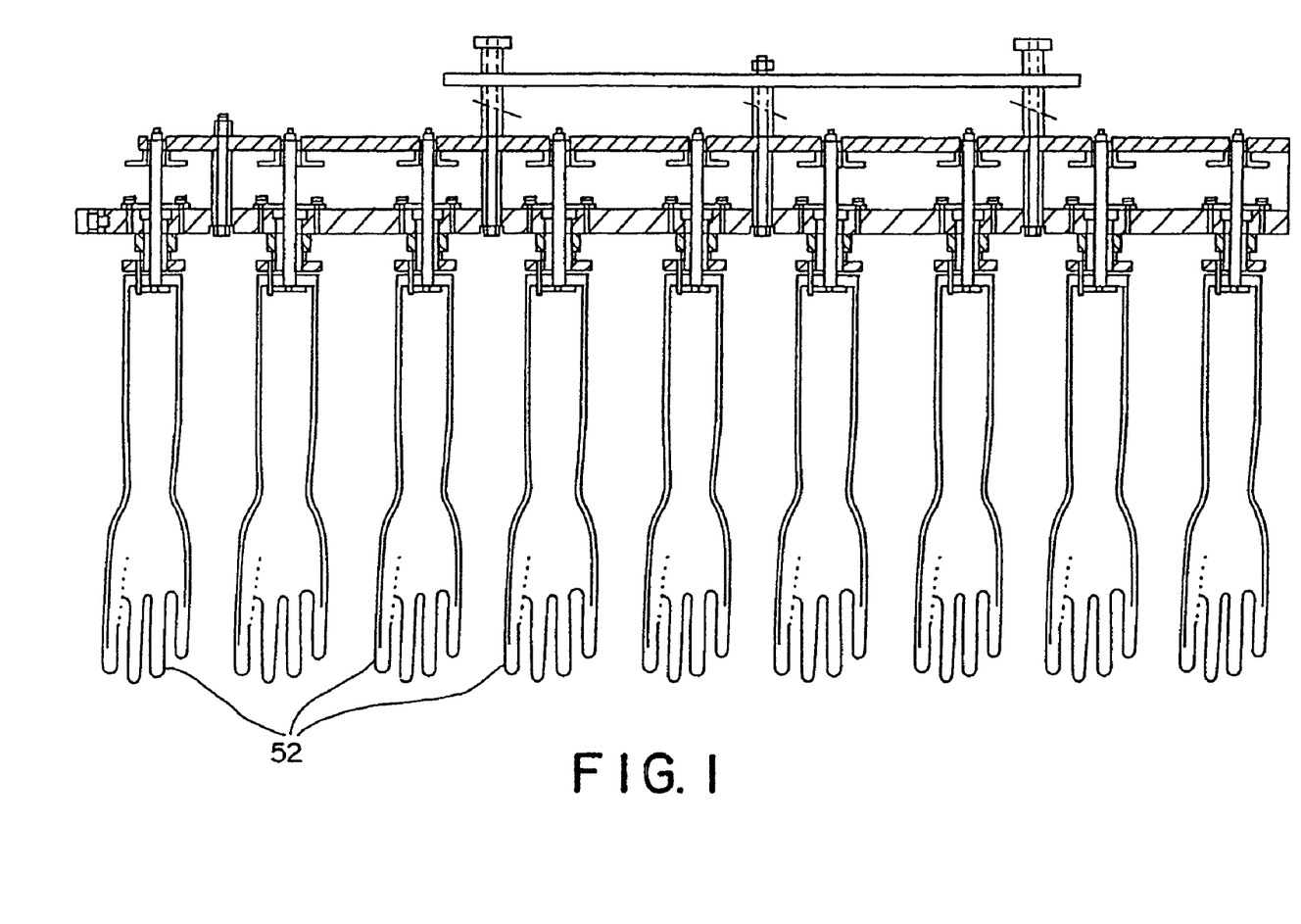
FIG. 1 is an illustration of glove-shaped formers that may be used in accordance with one embodiment of the present disclosure.

The elastomeric glove may be formed by a series of dipping processes of a former of the shape of the finished article. FIG. 1 is an illustration of a series of glove molds or formers 52 which may be used to form the gloves of the present disclosure. The formers 52 shown in FIG. 1 are illustrated on a pallet as is conventionally used in a batch processing operation, but it should be understood that the process of the present disclosure may equally be utilized in a continuous operation. A former 52 may generally be a contoured mold having a textured or smooth surface which may accept a series of coatings and release the formed article. Possible materials for the surface of former 52 may include any suitable surface material. For example, the surface of former 52 may be formed of ceramic, porcelain, glass, metal, or certain fluorocarbons.

If desired, a former may be cleaned prior to formation of a glove on the former. The cleaning process may generally include an optional water pre-rinse followed by an acid wash. After the acid wash, the former may be rinsed with water and dipped in a heated caustic solution prior to a final water rinse. After the cleaning process, a glove may be formed on the former through a series of dipping and drying steps.

Figure 2:
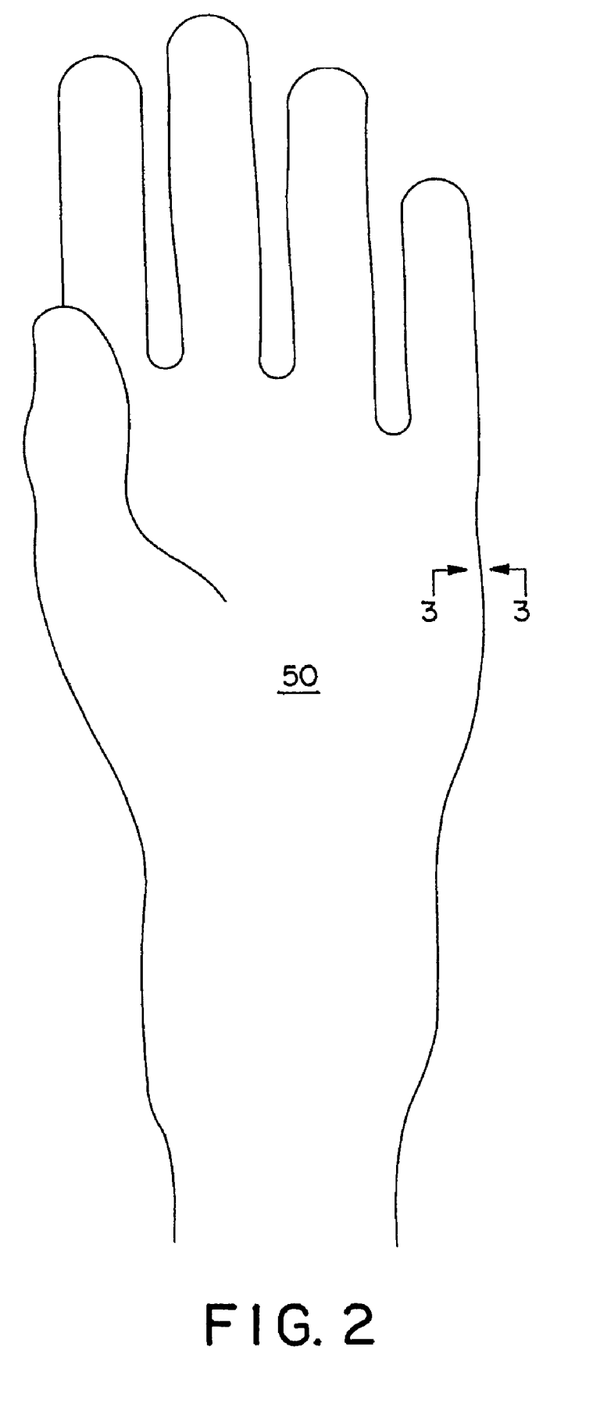
FIG. 2 is a front view of a glove according to the present disclosure.

FIG. 2 illustrates one possible embodiment of a glove 50 which may be formed on former 52. In one embodiment, the glove 50 may be formed through a series of dippings or immersions of the former 52. For example, a former release coating can be formed on the former prior to formation of the main body of the elastomeric article. A former release coating may prevent excessive adhesion between the former and the glove, improving the stripping ability of the glove. In one embodiment, a polymeric former release coating may be formed according to the processes of the present disclosure prior to formation of any other coatings on the former. A former release coating may optionally include other additives, such as a coagulant composition, for instance.

In one embodiment, after cleaning and the formation of a former release coating, when desired, the former 52 may be dipped into a coagulant composition prior to forming the main body or primary matrix of the glove on the former. For purposes of this disclosure, the primary matrix of the glove is defined to be the main body of the glove and includes one or more layers of elastomeric material. A coagulant causes a base latex polymer which may form the primary matrix of the glove to coagulate. Coagulants that may be used in the present disclosure may include powders, to ease stripping of the glove from the former, or, if desired, may be powder free coagulant compositions. In one embodiment, a powder free coagulant composition may be used which includes water soluble salts of calcium, zinc, aluminum, and the like. For example, in one embodiment, calcium nitrate in water or alcohol may be used in the coagulant composition. In such an embodiment, calcium nitrate may be present in the solution in an amount of up to about 40% by weight. Optionally, the coagulant composition may also contain additives such as surfactants.

After being immersed in the coagulant composition, the former is withdrawn and the coagulant present on the surface of the former is permitted to dry. For many applications, the coagulant may be air dried for a time of from about one minute to about two minutes. Once dried, a residual coating of the coagulant is left on the former.

If desired, the coagulant composition may contain certain additives. For example, the coagulant composition may contain various additives which may improve the tactile or other characteristics of a surface of the glove.

In one embodiment, after the coagulant dip, the former may be immersed or dipped into a latex emulsion of the desired elastomeric polymer. A latex is defined for the purposes of this disclosure as a colloid in which the elastomeric polymer is suspended in water.

In general, a latex emulsion of the present disclosure may have a dry rubber content (DRC) of less than about 50% or alternatively a total solid content (TSC) of less than about 50%. In one embodiment, a latex emulsion may have a DRC or a TSC content of less than about 25%. A latex emulsion may also contain various additives such as pH adjustors, stabilizers, and the like as are generally known in the art.

Upon contact of the latex with the coagulant composition, the coagulant may cause some of the latex to become locally unstable and coagulate on the surface of the former. Any additives in the coagulant composition may, depending upon what they are, form a layer between the former and the latex film such as a former release layer, for example, or alternatively may be incorporated into the latex film and may subsequently be removed during a leaching process. After the desired amount of time, the former is withdrawn from the latex emulsion, and the coagulated layer is allowed to coalesce fully on the former.

The amount of time the former is immersed in the emulsion (commonly termed "dwell time") determines the thickness of the film. Increasing the dwell time of the former in the latex causes the thickness of the film to increase. The total thickness of the film forming the glove body may depend on other parameters as well, including, for example, the solids content of the latex emulsion and the additive content of the latex emulsion and/or the coagulant composition.

After being dipped into the latex emulsion, the former is then heated to cure the polymer.

The elastomeric article of the present disclosure need not be formed from a coagulated latex emulsion. For example, in one embodiment, the elastomeric article of the present disclosure may be formed of a polymer which has been dissolved in a suitable solvent and then allowed to dry on a former in the desired shape as the solvent is evaporated from the solution. For example, one or more unsaturated block copolymers as are generally known in the art may be dissolved in a solvent, such as toluene, and may then be dried on a former in the shape of the desired elastomeric article. In one embodiment, styrene-isoprene-styrene (S-I-S) block copolymers, styrene-polybutadiene block copolymers (S-B), styrene-polybutadiene-styrene (S-B-S) block copolymers, and mixtures thereof can form the primary matrix of the glove. In one embodiment, the primary matrix of the glove can include a styrene-ethylene butylene-styrene (S-EB-S) block copolymer.

Various processing techniques as are generally known in the art may be incorporated into the present process. For example, an elastomeric layer may be gelled with heat to strengthen the elastomeric rubber film. If desired, the elastomeric layer may be leached with flowing hot water. A leaching process may extract various undesired constituents from the layer. This may cause the layer to shrink somewhat on the former and remove impurities. In one embodiment of the present disclosure, additional layers can be formed on the elastomeric base layer, such that the primary matrix of the glove includes multiple layers. Such a process is generally termed an over-dip process. In one embodiment, an over-dip process may be carried out by immersing the former including the base layer coating into an emulsion or a solution of a desired polymer. Additional layers on the primary matrix may, for instance, enhance certain characteristics of the glove. In one embodiment, the primary matrix of the glove may include an S-EB-S block copolymer layer and an over-dip layer of one or more other block copolymers, including, for example, S-I-S block copolymers, S-B block copolymers, and/or S-B-S block copolymers.

Once the primary matrix is formed on the former, the elastomeric materials may be dried and/or cured if necessary. The elastomeric materials may be cured by heating the primary matrix while on the former. For instance, the elastomeric materials may be heated to temperatures from about 100° C. to about 150° C. During curing, depending upon the elastomeric materials used, the elastomeric material may be vulcanized. During vulcanization, the polymer chains crosslink. In addition to curing the polymer coating, the high temperature process may also cause evaporation of any volatile components remaining on the former, including any remaining water.

After the primary matrix is formed, dried and optionally cured, the former is then dipped into a prepolymer composition for forming the foam layer. As described above, the prepolymer composition may comprise a polyurethane prepolymer, such as a polyisocyanate-capped polyoxyethylene polyol.

The prepolymer composition may contain the polyurethane prepolymer contained in any suitable diluent. The diluent, for instance, may comprise any non-aqueous diluent that does not interfere with the ability of the prepolymer composition to form a coating on the former. The diluent may comprise, for instance, N,N-dimethylformamide (DMF), tetrahydrofuran (THF), toluene, acetone, and the like. The diluent is combined with the polyurethane prepolymer in order to form a solution or emulsion that has the proper viscosity and other characteristics desired for a dip forming process.

The amount of polyurethane prepolymer contained in the diluent can depend upon various factors. For instance, the concentration of the prepolymer in the diluent can depend upon the particular prepolymer used and the desired viscosity. In general, however, the prepolymer and the diluent are combined together in amounts sufficient to permit dip forming of articles from the resulting solution or dispersion.

Once the prepolymer composition forms a coating on the former, in order to form the foam layer, the coating is contacted with a solution containing water and possibly one or more surfactants. The water can be contacted with the prepolymer coating in any suitable manner. For example, the aqueous solution can be sprayed on the former, the former can be dipped into the aqueous solution, or the prepolymer coating can simply be reacted with moisture contained in the surrounding environment. In still another embodiment, steam may be applied to the former for contacting the prepolymer coating with water.

The amount of aqueous solution that contacts the prepolymer coating can be carefully controlled in various embodiments for controlling the thickness of the resulting foam layer. Further, as described above, various surfactants can also be incorporated into the aqueous solution for controlling the properties of the foam.

The resulting foam, for instance, can be hydrophilic and can readily absorb water. The foam can also be formed so as to be lubricious. Further, the rigidity of the foam can also be controlled by controlling the different reactants and their relative concentrations.

After the foam layer is formed, if desired, the foam layer can be dried and the glove can be stripped from the former.

Figure 3:
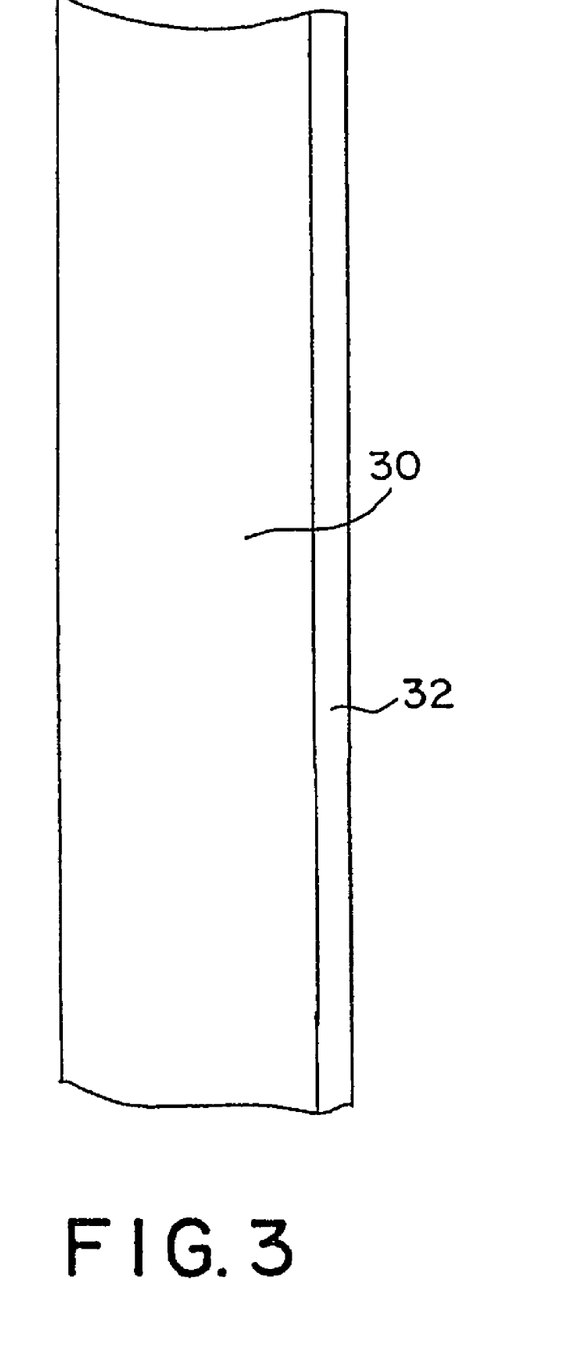
FIG. 3 is an enlarged cross-sectional view of one embodiment of an elastomeric article of the present disclosure.

FIG. 3 is an illustration of a cross section of a portion of one embodiment of an article made according to the present disclosure. In this particular embodiment, the primary matrix 30 of the glove is a single layer primary matrix. The foam layer 32 is applied to the surface of the primary matrix. As described above, the foam layer 32 generally forms a donning layer of the glove. When present, the foam layer can be configured to absorb water for preventing moisture from being trapped between the user's skin and the primary matrix 30.

The thickness of the foam layer can vary depending upon the particular application and the desired result. In FIG. 3, for instance, the foam layer 32 is shown to have a thickness less than the thickness of the primary matrix 30. It should be understood, however, that in other embodiments, the foam layer 32 may actually be thicker than the primary matrix 30. For instance, in various embodiments, the thickness of the foam layer may be less than about 50 microns. In other embodiments, however, the thickness may be greater than about 50 microns.

The foam layer once formed inside the glove can cover the entire interior surface of the glove or may only cover a portion of the glove. For instance, in one embodiment, the foam layer may only cover the palm portion of the glove or, alternatively, may cover the palm portion of the glove and the back of the glove without being located in the finger areas.

In addition, the thickness of the foam layer may vary over the interior surface of the glove. For instance, the foam layer may be thicker at the palm portion of the glove than at other locations.

In general, the prepolymer composition will adhere to any suitable elastomeric material. In one embodiment, however, various steps can be taken in order to improve the bond between the resulting foam layer and the primary matrix. For example, in one embodiment, the surface of the primary matrix may be treated with plasma or a chemical composition that creates amine groups, such as amino groups on the outside surface. Depending upon the prepolymer composition chosen, the amine groups can form covalent bonds with the foam layer.

These and other modifications and variations to the present disclosure may be practiced by those of ordinary skill in the art, without departing from the spirit and scope of the present disclosure, which is more particularly set forth in the appended claims. Furthermore, those of ordinary skill in the art will appreciate that the foregoing description is by way of example only, and is not intended to limit the disclosure so further described in such appended claims.

What is claimed:

1. A glove comprising:
   a primary matrix comprising an elastomeric polymer, the primary matrix being in the shape of a glove, the glove having an inside hand-contacting surface and an exterior surface wherein the primary matrix comprising an elastomeric polymer comprises the exterior surface of the glove such that the elastomeric polymer forms an outermost surface of the glove; and
   a donning layer located on the inside surface of the glove, the donning layer comprising a foam layer wherein the foam layer is hydrophilic and absorbs liquid moisture and transports it away from the hand-contacting surface such that liquid moisture does not remain in contact with a user's skin.

2. A glove as defined in claim 1, wherein the foam layer comprises a polyurethane foam.

3. A glove as defined in claim 1, wherein the foam layer comprises an open cell foam.

4. A glove as defined in claim 1, wherein the primary matrix comprises a nitrile polymer.

5. A glove as defined in claim 1, wherein the primary matrix comprises a natural rubber latex polymer.

6. A glove as defined in claim 1, wherein the primary matrix comprises a polyvinyl chloride polymer.

7. A glove as defined in claim 1, wherein the primary matrix comprises a block copolymer.

8. A glove as defined in claim 1, wherein the primary matrix comprises more than one layer.

9. A glove as defined in claim 1, wherein the foam layer is made from a material comprising a polyether polyurethane.

10. A glove as defined in claim 1, wherein the foam layer contains an additive incorporated into the foam layer, the additive comprising a material selected from the group consisting of anti-microbial agents, bacteriostatic agents, liquid absorption agents, medicaments, therapeutic agents, and mixtures thereof.

11. A glove as defined in claim 10, wherein the additive comprises an anti-microbial agent.

12. A glove as defined in claim 11, wherein the anti-microbial agent comprises a composition comprising silver.

13. A glove as defined in claim 10, wherein the additive comprises aloe.

14. A glove as defined in claim 1, wherein the foam layer comprises a reaction product of a prepolymer with a solution comprising water, the prepolymer comprising an isocyanate-capped polyoxyethylene polyol.

15. A glove as defined in claim 14, wherein the solution comprises water and at least one surfactant.

* * * * *